(12) United States Patent
    Craig

(10) Patent No.: US 11,771,902 B2
(45) Date of Patent: Oct. 3, 2023

(54) SYNCHRONIZATION OF VAGUS NERVE STIMULATION WITH THE CARDIAC CYCLE OF A PATIENT

(71) Applicant: Arthur Craig, Phoenix, AZ (US)

(72) Inventor: Arthur Craig, Phoenix, AZ (US)

(73) Assignee: DIGNITY HEALTH, Phoenix, AZ (US)

( * ) Notice: Subject to any disclaimer, the term of this patent is extended or adjusted under 35 U.S.C. 154(b) by 158 days.

(21) Appl. No.: 17/091,177

(22) Filed: Nov. 6, 2020

(65) Prior Publication Data

US 2021/0052902 A1    Feb. 25, 2021

Related U.S. Application Data

(63) Continuation of application No. 14/248,893, filed on Apr. 9, 2014, now Pat. No. 10,835,749, which is a continuation of application No. 12/401,026, filed on Mar. 10, 2009, now Pat. No. 8,738,126, which is a
(Continued)

(51) Int. Cl.
    | | |
    |---|---|
    | *A61N 1/36* | (2006.01) |
    | *A61B 5/0205* | (2006.01) |
    | *A61B 5/349* | (2021.01) |
    | *A61N 1/05* | (2006.01) |
    | *A61B 5/00* | (2006.01) |
    | *A61B 5/369* | (2021.01) |
    | *A61B 5/352* | (2021.01) |

(Continued)

(52) U.S. Cl.
    CPC ........ *A61N 1/36139* (2013.01); *A61B 5/0205* (2013.01); *A61B 5/349* (2021.01); *A61N 1/0551* (2013.01); *A61N 1/3605* (2013.01); *A61N 1/3611* (2013.01); *A61N 1/36053* (2013.01); *A61N 1/36064* (2013.01); *A61N 1/36082* (2013.01); *A61N 1/36114* (2013.01); *A61N 1/36178* (2013.01); *A61B 5/352* (2021.01); *A61B 5/353* (2021.01); *A61B 5/355* (2021.01); *A61B 5/369* (2021.01); *A61B 5/4094* (2013.01)

(58) Field of Classification Search
    None
    See application file for complete search history.

(56) References Cited

U.S. PATENT DOCUMENTS

| | | |
|---|---|---|
| 4,073,048 A | 2/1978 | Ditcher |
| 5,073,048 A | 12/1991 | Adachi et al. |
| 5,150,508 A | 9/1992 | St Denis |

(Continued)

*Primary Examiner* — Erica S Lee
(74) *Attorney, Agent, or Firm* — CF3; Stephen Eisenmann

(57) ABSTRACT

Disclosed herein are methods, systems, and apparatus for treating a medical condition of a patient, involving detecting a physiological cycle or cycles of the patient and applying an electrical signal to a portion of the patient's vagus nerve through an electrode at a selected point in the physiological cycle(s). The physiological cycle can be the cardiac and/or respiratory cycle. The selected point can be a point in the cardiac cycle correlated with increased afferent conduction on the vagus nerve, such as a point from about 10 msec to about 800 msec after an R-wave of the patient's ECG, optionally during inspiration by the patient. The selected point can be a point in the cardiac cycle when said applying increases heart rate variability, such as a point from about 10 msec to about 800 msec after an R-wave of the patient's ECG, optionally during expiration by the patient.

13 Claims, 10 Drawing Sheets

Related U.S. Application Data continuation of application No. 11/693,499, filed on Mar. 29, 2007, now Pat. No. 8,219,188.

(60) Provisional application No. 60/787,680, filed on Mar. 29, 2006.

(51) Int. Cl.
*A61B 5/353* (2021.01)
*A61B 5/355* (2021.01)

(56) References Cited

U.S. PATENT DOCUMENTS

| | | | |
|---|---|---|---|
| 5,928,272 A * | 7/1999 | Adkins | A61N 1/36064 607/45 |
| 6,104,959 A | 8/2000 | Spertell | |
| 6,115,627 A * | 9/2000 | Street | A61B 5/366 600/515 |
| 6,141,590 A * | 10/2000 | Renirie | A61N 1/36564 607/18 |
| 6,631,293 B2 | 10/2003 | Lyden | |
| 6,737,875 B2 | 5/2004 | Davis et al. | |
| 6,754,530 B2 | 6/2004 | Bakels et al. | |
| 6,788,975 B1 | 9/2004 | Whitehurst et al. | |
| 6,825,767 B2 | 11/2004 | Humbard | |
| 6,843,870 B1 | 1/2005 | Bluger | |
| 6,900,421 B2 | 5/2005 | Varma | |
| 6,901,292 B2 | 5/2005 | Hrdlicka et al. | |
| 6,901,293 B2 | 5/2005 | Rogers et al. | |
| 6,940,255 B2 | 9/2005 | Loch | |
| 6,949,929 B2 | 9/2005 | Gray et al. | |
| 6,958,705 B2 | 10/2005 | Lebel et al. | |
| 7,076,307 B2 | 7/2006 | Boveja et al. | |
| 7,085,605 B2 | 8/2006 | Bluger et al. | |
| 7,107,097 B2 | 9/2006 | Stern et al. | |
| 7,142,923 B2 | 11/2006 | North et al. | |
| 7,149,574 B2 | 12/2006 | Yun et al. | |
| 7,164,941 B2 | 1/2007 | Misczynski et al. | |
| 7,184,837 B2 | 2/2007 | Goetz | |
| 7,191,012 B2 | 3/2007 | Boveja et al. | |
| 7,209,790 B2 | 4/2007 | Thompson et al. | |
| 7,236,822 B2 | 6/2007 | Dobak, III | |
| 7,239,912 B2 | 7/2007 | Dobak, III | |
| 7,239,926 B2 | 7/2007 | Goetz | |
| 7,249,281 B2 | 7/2007 | Shirley et al. | |
| 7,252,090 B2 | 8/2007 | Goetz | |
| 7,254,439 B2 | 8/2007 | Misczynski et al. | |
| 7,263,405 B2 | 8/2007 | Boveja et al. | |
| 7,277,758 B2 | 10/2007 | DiLorenzo | |
| 7,289,844 B2 | 10/2007 | Misczynski et al. | |
| 7,292,890 B2 | 11/2007 | Whitehurst et al. | |
| 7,299,091 B2 | 11/2007 | Barrett et al. | |
| 7,321,793 B2 | 1/2008 | Ben Ezra et al. | |
| 7,340,306 B2 | 3/2008 | Barrett et al. | |
| 7,346,395 B2 | 3/2008 | Lozano et al. | |
| 7,363,076 B2 | 4/2008 | Yun et al. | |
| 7,369,897 B2 | 5/2008 | Boveja et al. | |
| 7,377,930 B2 | 5/2008 | Loughran | |
| 7,395,117 B2 | 7/2008 | Mazar et al. | |
| 7,418,292 B2 | 8/2008 | Shafer | |
| 7,444,183 B2 | 10/2008 | Knudson et al. | |
| 7,444,184 B2 | 10/2008 | Boveja et al. | |
| 7,454,281 B2 | 11/2008 | Rezai et al. | |
| 7,454,359 B2 | 11/2008 | Rosenfeld et al. | |
| 7,483,743 B2 | 1/2009 | Mann et al. | |
| 7,485,095 B2 | 2/2009 | Shusterman | |
| 7,493,168 B2 | 2/2009 | Rezai | |
| 7,496,409 B2 | 2/2009 | Greenhut et al. | |
| 7,512,438 B2 | 3/2009 | Fischell et al. | |
| 7,519,430 B2 | 4/2009 | Von Arx et al. | |
| 7,532,938 B2 | 5/2009 | Machado et al. | |
| 7,542,800 B2 | 6/2009 | Libbus et al. | |
| 8,467,876 B2 * | 6/2013 | Tehrani | A61N 1/36132 607/42 |
| 2004/0193231 A1 * | 9/2004 | David | A61B 5/4029 607/48 |
| 2004/0199210 A1 * | 10/2004 | Shelchuk | A61N 1/36114 607/17 |
| 2004/0254616 A1 | 12/2004 | Rossing et al. | |
| 2005/0197675 A1 | 9/2005 | David et al. | |
| 2005/0251216 A1 * | 11/2005 | Hill | A61N 1/056 607/9 |
| 2006/0015153 A1 | 1/2006 | Gliner et al. | |
| 2006/0095090 A1 * | 5/2006 | De Ridder | A61N 1/0553 607/57 |
| 2006/0206155 A1 * | 9/2006 | Ben-David | A61N 1/3962 607/9 |
| 2007/0179557 A1 * | 8/2007 | Maschino | A61N 2/008 607/45 |

* cited by examiner

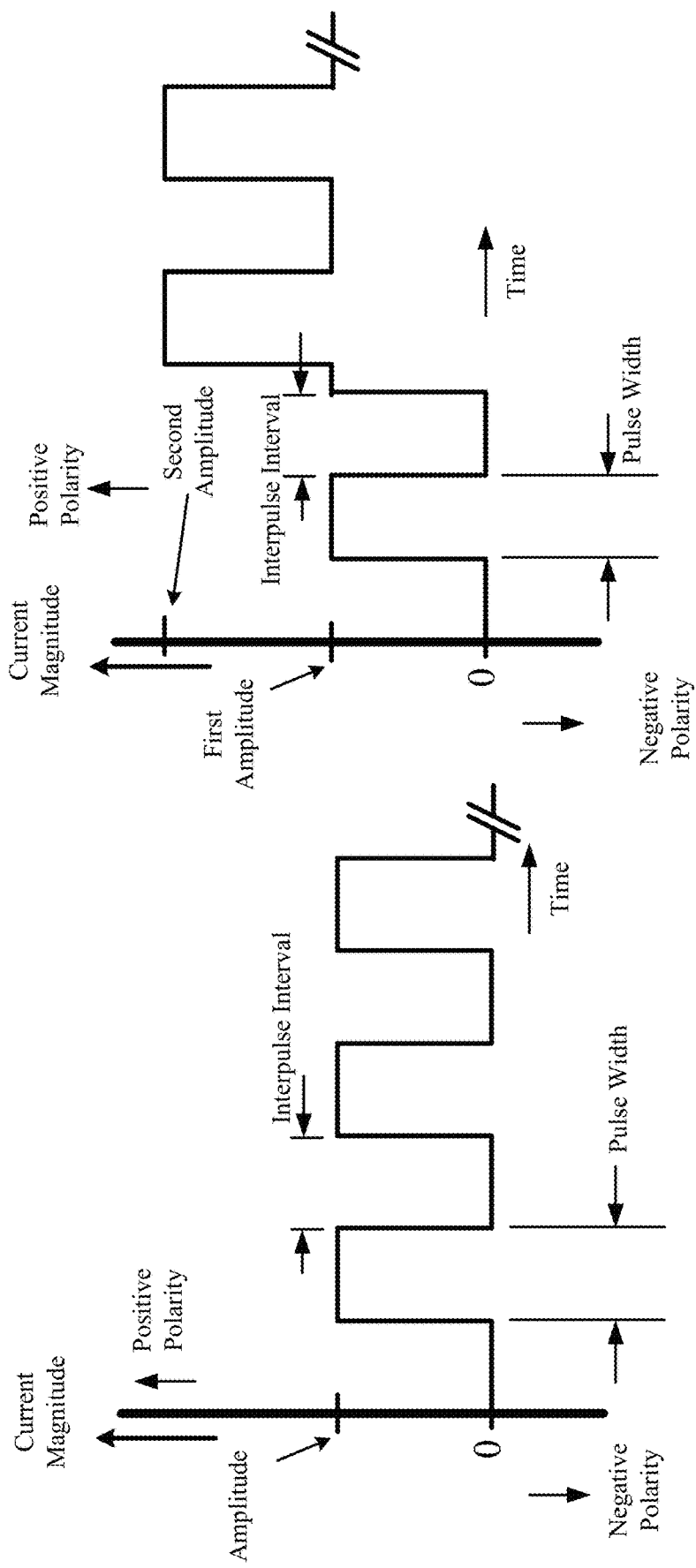

SYNCHRONIZATION OF VAGUS NERVE STIMULATION WITH THE CARDIAC CYCLE OF A PATIENT

BACKGROUND OF THE INVENTION

The present application claims priority to and is a continuation of U.S. patent application Ser. No. 14/248,893, filed on Apr. 9, 2014 (Now U.S. Pat. No. 10,835,749), entitled "Synchronization of Vagus Nerve Stimulation with the Cardiac Cycle of a Patient," which claims priority to and is a continuation of U.S. patent application Ser. No. 12/401, 026, filed on Mar. 10, 2009 (now U.S. Pat. No. 8,738,126), entitled "Synchronization of Vagus Nerve Stimulation with the Cardiac Cycle of a Patient," which claims priority to and is a continuation of U.S. patent application Ser. No. 11/693, 499, filed on Mar. 29, 2007 (now U.S. Pat. No. 8,219,188), entitled "Synchronization of Vagus Nerve Stimulation with the Cardiac Cycle of a Patient," which claims priority to U.S. provisional patent application No. 60/787,680, filed on Mar. 29, 2006, all of which are incorporated in their entireties herein by reference.

FIELD OF THE INVENTION

This invention relates generally to medical device systems and, more particularly, to medical device systems for applying electrical signals to a cranial nerve for the treatment of medical conditions, and for improved electrical signals in such systems.

DESCRIPTION OF THE RELATED ART

Many advancements have been made in treating diseases such as depression and epilepsy. Therapies using electrical signals for treating these diseases have been found to effective. Implantable medical devices have been effectively used to deliver therapeutic stimulation to various portions of the human body (e.g., the vagus nerve) for treating these diseases. As used herein, "stimulation" or "stimulation signal" refers to the application of an electrical, mechanical, magnetic, electro-magnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a medical condition by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking of the conduction of action potentials, whether endogenous or exogenously induced, including hyperpolarizing and/or collision blocking, (c) affecting changes in neurotransmitter/neuromodulator release or uptake, and (d) changes in neuroplasticity or neurogenesis of brain tissue.

In some embodiments, electrical neurostimulation may be provided by implanting an electrical device underneath the skin of a patient and delivering an electrical signal to a nerve such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may apply a series of electrical pulses to the nerve (e.g., a cranial nerve such as a vagus nerve) periodically, intermittently, or continuously throughout the day, or over another predetermined time interval. This type of stimulation is generally referred to as "passive," "non-feedback," or "prophylactic," stimulation. The electrical signal may be applied by an IMD that is implanted within the patient's body. In other cases, the signal may be generated by an external pulse generator outside the patient's body, coupled by an RF or wireless link to an implanted electrode.

Generally, neurostimulation signals that perform neuromodulation are delivered by the IMD via one or more leads. The leads generally terminate at their distal ends in one or more electrodes, and the electrodes, in turn, are electrically coupled to tissue in the patient's body. For example, a number of electrodes may be attached to various points of a nerve or other tissue inside a human body for delivery of a neurostimulation signal.

While feedback stimulation schemes have been proposed, conventional vagus nerve stimulation (VNS) usually involves non-feedback stimulation characterized by a number of parameters. Specifically, convention vagus nerve stimulation usually involves a series of electrical pulses in bursts defined by an "on-time" and an "off-time." During the on-time, electrical pulses of a defined electrical current (e.g., 0.5-2.0 milliamps) and pulse width (e.g., 0.25-1.0 milliseconds) are delivered at a defined frequency (e.g., 20-30 Hz) for the on-time duration, usually a specific number of seconds, e.g., 10-100 seconds. The pulse bursts are separated from one another by the off-time, (e.g., 30 seconds-5 minutes) in which no electrical signal is applied to the nerve. The on-time and off-time parameters together define a duty cycle, which is the ratio of the on-time to the combination of the on-time and off-time, and which describes the percentage of time that the electrical signal is applied to the nerve.

In conventional VNS, the on-time and off-time may be programmed to define an intermittent pattern in which a repeating series of electrical pulse bursts are generated and applied to the vagus nerve. Each sequence of pulses during an on-time may be referred to as a "pulse burst." The burst is followed by the off-time period in which no signals are applied to the nerve. The off-time is provided to allow the nerve to recover from the stimulation of the pulse burst, and to conserve power. If the off-time is set at zero, the electrical signal in conventional VNS may provide continuous stimulation to the vagus nerve. Alternatively, the idle time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in conventional VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-150 Hz (i.e., 20 pulses per second to 150 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Various feedback stimulation schemes have been proposed. In U.S. Pat. No. 5,928,272, the automatic activation of a neurostimulator such as a vagus nerve stimulator is described based on a detected increase in heart rate. The '272 patent notes that epilepsy attacks are sometimes preceded by increases in heart rate and proposes automatically applying an electrical signal to a vagus nerve if the patient's heart rate exceeds a certain level. The patent does not disclose initiating or synchronizing the therapeutic electrical signal with the patient's heart rhythms. Instead, detection of an abnormal heart rate is used to trigger otherwise conventional VNS.

A new type of stimulation has been proposed known as "microburst" stimulation, which provides enhanced evoked potentials in the brain (as more fully described in co-pending application Ser. No. 14/089,185, "Microburst Electrical Stimulation Of Cranial Nerves For The Treatment Of Medical Conditions"). "Enhanced" in this context refers to electrical potentials evoked in the forebrain by neurostimulation that are higher than those produced by conventional neurostimulation. The electrical signal for this improved therapy is substantially different from the electrical signals in conventional VNS. In particular, electrical signals in microburst stimulation are characterized by very short bursts of a limited number of electrical pulses. These shorts bursts of less than 1 second are referred to hereinafter as "microbursts." By applying an electrical signal comprising a series of microbursts to, for example, a vagus nerve of a patient, enhanced vagal evoked potentials (eVEP) are produced in therapeutically significant areas of the brain. Significantly, eVEP are not produced by conventional vagus nerve stimulation.

As used herein, the term "microburst" refers to a portion of a therapeutic electrical signal comprising a limited plurality of pulses and a limited burst duration. More particularly, a microburst may comprise at least two but no more than 25 electrical pulses, and may last for no more than 1 second, and typically less than 100 milliseconds, more typically 10-80 msec. A therapeutic electrical signal may comprise a series of microbursts separated from one another by time intervals known as "interburst periods" which allow a refractory interval for the nervous system to recover from the microburst and again become receptive to eVEP stimulation by another microburst. In some embodiments, the interburst period may be as long as or longer than the adjacent microbursts separated by the interburst period. In some embodiments the interburst period may comprise an absolute time period of at least 100 milliseconds and in some embodiments, up to 6 seconds. Adjacent pulses in a microburst are separated by a time interval known as an "interpulse interval," which may comprise a time period from 1 msec to 50 msec. The interpulse interval, together with the number of pulses and the pulse width of each pulse, determines a "microburst duration," which is the length of a microburst from the beginning of the first pulse to the end of the last pulse (and thus the beginning of a new interburst period). Microburst duration in microburst stimulation can be 1 second or less (i.e., microbursts can be no greater than 1 second), and more preferably is 100 msec or less, and still more preferably is in the range of 10-80 msec. The pulses in a microburst may be further characterized by a current amplitude and a pulse width. Microburst stimulation may optionally include an on-time and an off-time in which the microbursts are provided and not provided, respectively, to a cranial nerve. At least one of the interburst period, the number of pulses per burst, the interpulse interval, the microburst duration, the current amplitude, the pulse width, the on-time, or the off-time are selected to enhance cranial nerve evoked potentials.

The timing of neurostimulation signals has heretofore generally conformed to standard clock cycles, without regard to the efficacy of neurostimulation signals delivered at particular time-points. The present inventor is unaware of previous investigations of the efficacy of neurostimulation signals delivered at particular time-points of physiological cycles.

SUMMARY OF THE INVENTION

In one embodiment, the present invention provides a method of treating a medical condition of a patient using an implantable medical device, comprising detecting said patient's cardiac cycle and applying an electrical signal to a portion of a vagus nerve of said patient through an electrode at a selected point in the cardiac cycle, to treat the medical condition.

In one embodiment, the present invention is a method of treating a medical condition of a patient, comprising: coupling at least one electrode to at least one vagus nerve of the patient, providing a programmable electrical signal generator coupled to the electrode, detecting said patient's cardiac cycle, generating an electrical signal with the electrical signal generator, and applying the electrical signal to the electrode to treat the medical condition, and wherein the applying the electrical signal at a selected point in the cardiac cycle.

Applying an electrical signal at a selected point in a physiological cycle may be referred to herein as "synchronizing" the electrical signal with the physiological cycle. Synchronizing does not require modification of one or more electrical signal parameters to match one or more parameters of the physiological cycle.

In one embodiment, the present invention is a computer readable program storage device encoded with instructions that, when executed by a computer, perform a method comprising: detecting said patient's cardiac cycle, generating an electrical signal with the electrical signal generator, and applying the electrical signal to an electrode coupled to at least one vagus nerve of the patient to treat the medical condition, and wherein applying the electrical signal to the vagus nerve occurs at a selected point in the cardiac cycle.

In one aspect, the present invention relates to a medical condition treatment system comprising at least one electrode coupled to at least one vagus nerve of a patient, an implantable device operatively coupled to the electrode and comprising an electrical signal generator capable of applying an electrical signal to the vagus nerve at a selected point in the patient's cardiac cycle, and a device operatively coupled to the electrode and capable of detecting said patient's cardiac cycle.

In another alternate embodiment, the method may comprise alternating first and second time periods, wherein in the first time period a conventional vagus nerve stimulation electrical signal is applied to a vagus nerve of a patient, and a second time period in which microburst electrical signals are applied to a vagus nerve of a patient. The conventional vagus nerve stimulation signal may be defined by a current amplitude, a pulse width, a frequency, an on-time and an off-time. In one embodiment, the first time period (in which the conventional VNS electrical signal is applied to the vagus nerve) corresponds to the on-time and the second time period (in which the microburst electrical signal is applied to the vagus nerve), corresponds to the off-time of the conventional vagus nerve signal.

In any embodiment, the selected point in the cardiac cycle can be a point in the cardiac cycle correlated with increased afferent conduction on the vagus nerve, such as a point from about 10 msec to about 800 msec after an R-wave of the patient's ECG. In a particular embodiment, the selected point in the cardiac cycle occurs from about 10-800 msec after an R-wave during inspiration by the patient. In a different embodiment, the selected point in the cardiac cycle occurs from about 10-800 msec after an R-wave during expiration by the patient. In a further embodiment, the selected point in the cardiac cycle occurs from about 10-500 msec after an R-wave of the patient's ECG, which may further occur during inspiration, expiration, or without regard to respiration. In another embodiment, the selected point in the cardiac cycle can be a point in the cardiac cycle when said applying increases heart rate variability.

In one embodiment, the present invention is a method of treating a medical condition of a patient, comprising: coupling at least one electrode to at least one vagus nerve of the patient, providing a programmable electrical signal generator coupled to the electrode, detecting said patient's respiratory cycle, generating an electrical signal with the electrical signal generator, and applying the electrical signal to the electrode to treat the medical condition, and wherein the applying the electrical signal at a selected point in the respiratory cycle.

In a further embodiment, the present invention is a method of treating a medical condition of a patient, comprising: coupling at least one electrode to at least one vagus nerve of the patient, providing a programmable electrical signal generator coupled to the electrode, detecting said patient's respiratory cycle and cardiac cycle, generating an electrical signal with the electrical signal generator, and applying the electrical signal to the electrode to treat the medical condition, and wherein the applying the electrical signal at a selected point in the respiratory cycle and/or cardiac cycle.

BRIEF DESCRIPTION OF THE DRAWINGS

The invention may be understood by reference to the following description taken in conjunction with the accompanying drawings, in which like reference numerals identify like elements, and in which:

FIGS. 4A, 4B, and 4C illustrate exemplary waveforms for generating the electrical signals for stimulating the vagus nerve for treating a medical condition, according to one illustrative embodiment of the present invention;

Figure 1:
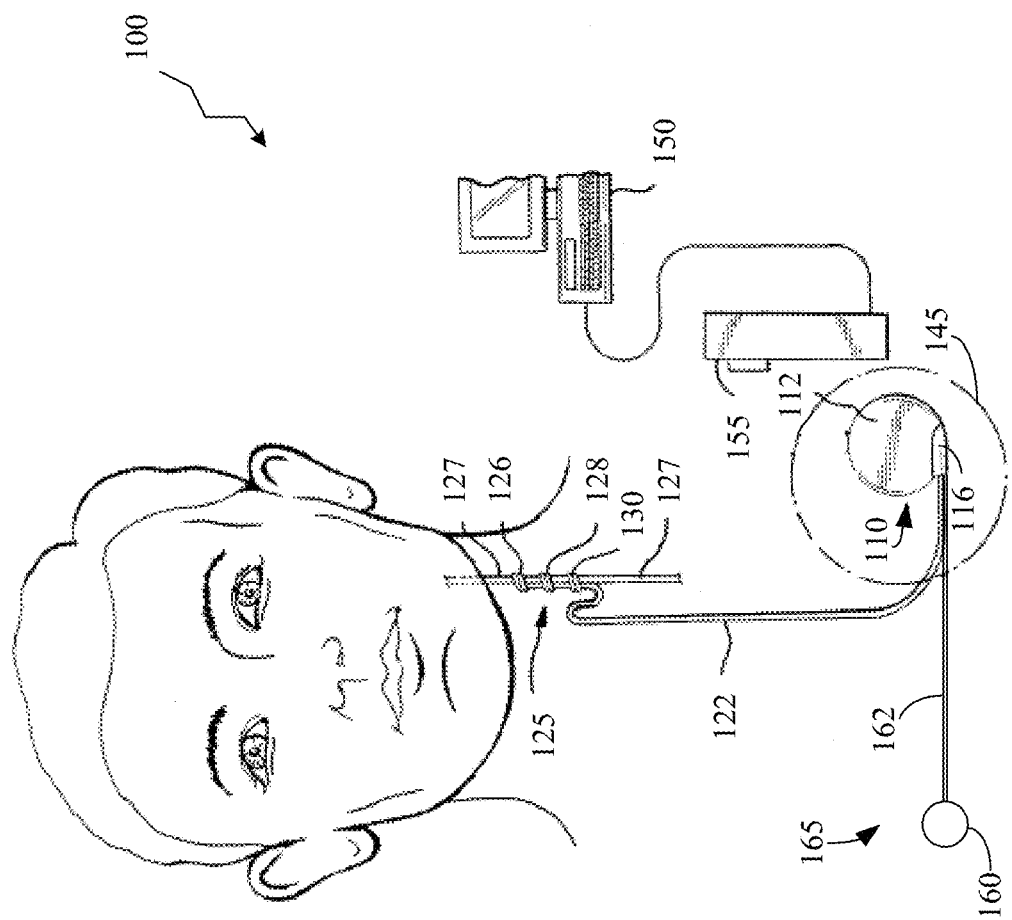
FIG. 1 provides a stylized diagram of an implantable medical device implanted into a patient's body for providing a therapeutic electrical signal to a neural structure of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

Cranial nerve stimulation has been proposed to treat a number of medical conditions pertaining to or mediated by one or more structures of the nervous system of the body, including epilepsy and other movement disorders, depression, anxiety disorders and other neuropsychiatric disorders, dementia, head trauma, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous medical conditions for which cranial nerve stimulation has been proposed or suggested as a treatment option, the fact that detailed neural pathways for many (if not all) cranial nerves remain relatively unknown, makes predictions of efficacy for any given medical condition difficult or impossible. Moreover, even if such pathways were known, the precise stimulation parameters that would modulate particular pathways relevant to a particular medical condition generally cannot be predicted.

In one embodiment, the present invention relates to a method of treating a medical condition selected from the group consisting of epilepsy, neuropsychiatric disorders (including but not limited to depression), eating disorders/ obesity, traumatic brain injury/coma, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, and reproductive endocrine disorders (including fertility) in a patient.

The present invention relates to synchronization of cranial nerve electrical stimulation to a physiological event, such as a specific point in the cardiac cycle and/or respiratory cycle. Synchronization of such electrical stimulation signals may, in one embodiment, be performed by an implantable medical device (IMD) system. An IMD system may comprise an implantable medical device for delivering a therapeutic electrical signal and sensing/recording data, and an external device (ED) capable of programming and/or data transfer operations with the IMD.

The medical device system of the present invention provides for software module(s) that are capable of acquiring, storing, and processing one or more forms of data, such as patient data/parameters (e.g., physiological data such as heart rate, cardiac cycle data and respiration cycle data, side-effects data, brain-activity data, disease progression or regression data, self-evaluation data, seizure characteristic data, quality of life data, etc.) and therapy parameter data. Therapy parameters may include, but are not limited to, electrical signal parameters that define the therapeutic electrical signals delivered by the medical device, medication parameters (e.g., dosages, frequency of medication provided to the patient, etc.) and/or any other therapeutic treatment parameter. In an alternative embodiment, the term "therapy parameters" may refer to electrical signal parameters defining the therapeutic electrical signals delivered by the medical device. Therapy parameters for a therapeutic electrical signal may also include, but are not limited to, an interburst period, a number of pulses per burst, an interpulse interval, a burst duration, a current amplitude, a pulse width, a pulse frequency, a signal on-time, a signal off-time, and/or a duty cycle.

Although not so limited, a system capable of implementing embodiments of the present invention is described below. FIG. 1 depicts a stylized implantable medical device (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes.

Lead assembly 122 is attached at its proximal end to connectors on the header 116 of generator 110. The electrode assembly 125 may be surgically coupled to a vagus nerve 127 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 125 comprises a bipolar stimulating electrode pair 126, 128 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve 127, and the electrode assembly 125 may be secured to the vagus nerve 127 by a spiral anchoring tether 130 such as that disclosed in U.S. Pat. No. 4,979,511 issued Dec. 25, 1990 to Reese S. Terry, Jr. and assigned to the same assignee as the instant application. Lead assembly 122 may be secured, while retaining the ability to flex with movement of the chest and neck, by a suture connection to nearby tissue (not shown).

In some embodiments, the electrode assembly 125 may comprise temperature sensing elements, heart rate or cardiac cycle sensor elements, and/or respiration cycle sensing elements. In one embodiment, the electrode assembly 125 comprises a strain gauge that may be used to determine inspiration by identifying chest expansion. By detecting the onset of chest expansion, the strain gauge may detect the onset of inspiration. The strain gauge may also detect expiration by identifying when the chest is contracting. Other sensors for other body parameters may also be employed to trigger active stimulation. Both passive and active stimulation may be combined or delivered by a single IMD according to the present invention. Either or both modes may be appropriate to treat a specific patient under observation.

In one embodiment, a sensor assembly 165, comprising a sensor lead assembly 162 and a sensor 160, may be employed to detect a body parameter of the patient, such as a parameter related to the patient's cardiac cycle. The sensor 160 may be one or more electrocardiogram leads or a heart rate monitor, among other sensing devices.

The electrical pulse generator 110 may be programmed with an external device (ED) such as computer 150 using programming software known in the art. A programming wand 155 may be coupled to the computer 150 as part of the ED to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

The IMD 100 may detect one or more portions of patient's cardiac cycle, e.g., P waves, R waves, R-R interval, QRS complex, T waves, etc., or the entire PQRST cycle. In response to detecting the one or more portions of the cardiac cycle, the IMD 100 may cause the pulse generator 110 to deliver an electrical signal via leads 122 to a cranial nerve such as vagus nerve 127 at a particular point during the cardiac cycle. For example, a sensor 160, such as a heart rate monitor or a set of electrocardiogram (ECG) leads, may be used to detect the one or more portions of the patient's cardiac cycle. The detected portion of the cardiac cycle may then be used to trigger the pulse generator 110 to generate the therapeutic electrical signal and apply the signal to the vagus nerve 127.

A "cardiac cycle" herein refers to the electrical activity of a patient's heart that occurs in the period between the onset of consecutive P waves. This electrical activity may be measured and analyzed by an electrocardiogram (ECG). The cycle begins with the P wave, which corresponds to electrical depolarization of the atria of the heart. As is known, an electrocardiogram exhibits a P wave, a QRS complex, and a T wave, and in some patients it may also exhibit a U wave. An isoelectric baseline follows from the end of the T or U wave to the onset of the next P wave with the patient's next heartbeat.

Figure 8:
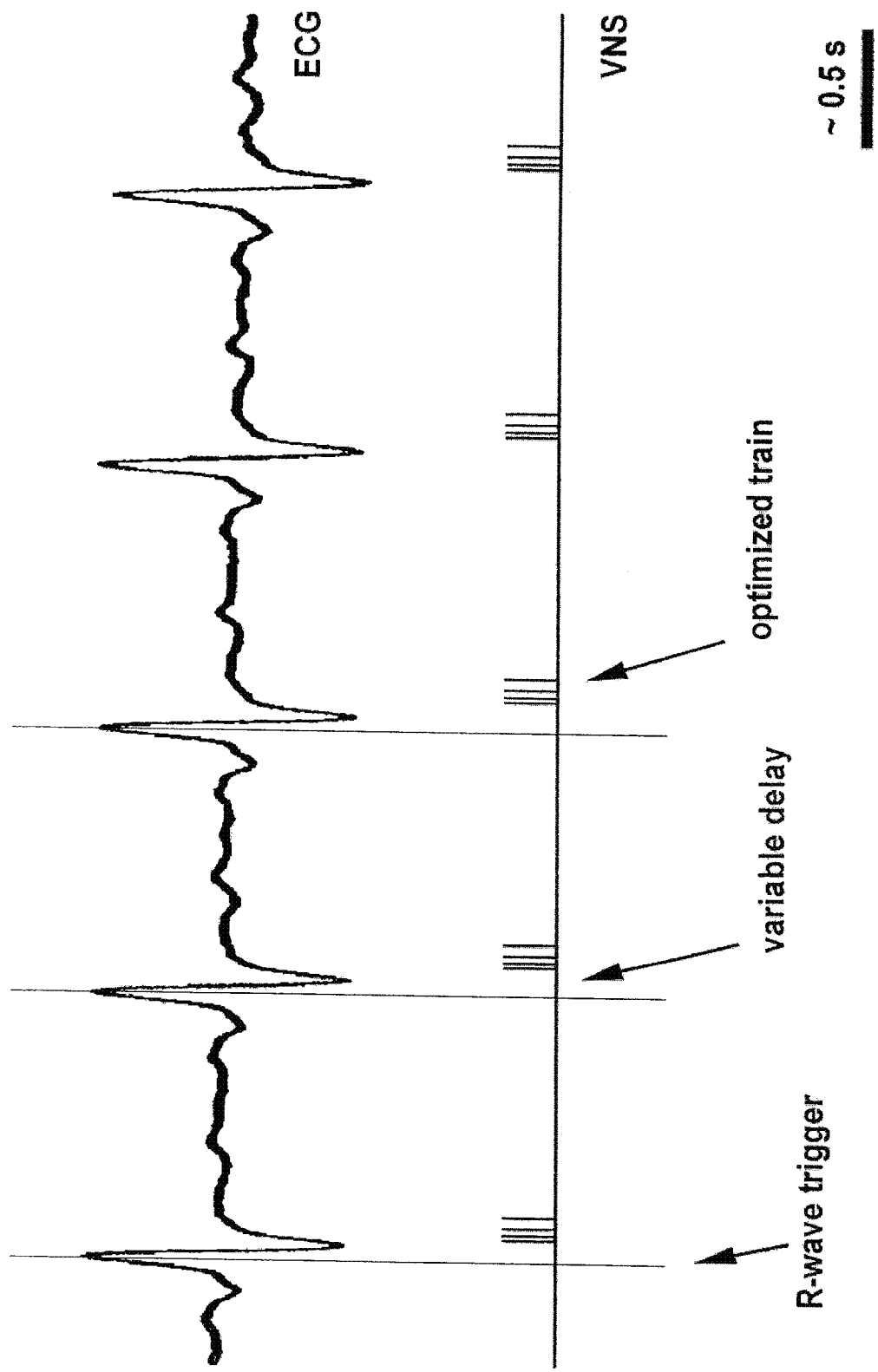
FIG. 8 illustrates synchronization of a vagal stimulus burst to the QRS wave of a patient's ECG.

According to one aspect of the present invention, conventional bursts and/or microbursts of electrical pulses comprising an electrical signal are applied to the vagus nerve in synchronization with one or more portions of the cardiac cycle. In one embodiment, the electrical signal is synchronized with the R wave of a patient's cardiac cycle. In another embodiment, the signal is synchronized with the QRS complex. In a further embodiment, the signal is further synchronized with the respiration cycle of the patient. In a still further embodiment, the therapeutic electrical signal is synchronized with both a portion of the patient's cardiac cycle and the respiration cycle of the patient. Synchronization of the application of the therapeutic electrical signal with the patient's cardiac and/or respiration cycles enables the IMD to augment endogenous cardiac-related and/or respiration-related vagal afferent activity with the exogenous electrical signal. In one embodiment, as illustrated in FIG. 8, the neurostimulation burst is triggered by the R-wave of the ECG after a delay period, which comprises a predetermined or random time interval that may range, e.g., from ~10-800 msec following detection of the R-wave. In another embodiment, the therapeutic electrical signal is applied to the vagus nerve after a predetermined or random time interval, e.g. ~10-1000 msec following the beginning of inspiration by the patient. In one further embodiment, the IMD 100 applies an electrical signal to a cranial nerve, such as vagus nerve 127, beginning at a point from about 10 msec to about 800 msec after an R-wave of the patient's ECG when the patient is inspiring. Without being bound by theory, it is believed that synchronizing the application of the exogenous therapeutic electrical signal to the vagus nerve with the detection of the R-wave of the patient's cardiac cycle and/or the beginning of inspiration by the patient may increase the efficacy of neurostimulation therapy by entraining the exogenous signal with the endogenous cyclic facilitation of central vagal afferent pathways.

In one embodiment, a first electrical signal is applied in synchrony with the patient's cardiac and/or respiratory cycles, as described above, and a second electrical signal is applied without reference to the patient's physiological cycle, wherein the second electrical signal differs from the first in at least one parameter selected from the group consisting of a burst duration, a number of pulses per burst, an interpulse interval, an interburst period, a current magnitude, a pulse frequency, a signal width, an on-time, and an off-time.

In another embodiment, the synchronization of the exogenous electrical signal further comprises not providing the exogenous signal during periods in the opposite half of the cardiac and/or respiratory duty cycles, when the central pathways are inhibited. Again without being bound by theory, it is believed that asynchronously-applied neurostimulation signals in other portions of the cardiac and/or respiratory cycles may be less effective because endogenous signals in those portions of the cardiac and/or respiratory cycles are less significant, in terms of their information content, for modulating those portions of the brain relevant to homeostasis mechanisms implicated in medical conditions such as epilepsy and depression, among others. Thus, at least a portion of the exogenous electrical signal in conventional stimulation algorithms may be therapeutically irrelevant, or even counterproductive.

Accordingly, in one embodiment, the therapeutic electrical signal burst or microburst is applied to the cranial nerve, such as the vagus nerve 127, after a delay period of, e.g., ~10-800 msec following detection of the R-wave, and no signal is applied during the remaining portions of one or more subsequent cardiac cycles. In another embodiment, the therapeutic electrical signal is applied to the vagus nerve after a delay period of ~10-1000 msec following the beginning of inspiration by the patient, and no signal is applied to the nerve during the remaining portions of the respiration cycle. In still another embodiment, the therapeutic electrical signal is applied to the vagus nerve after a delay period following detection of the R-wave only if the patient is inspiring, and otherwise no signal is applied to the vagus nerve.

A patient's heart rate can vary due to a number of reasons, including variations in activity level (e.g., exercise or other exertion), variations in emotional state, or variations in breathing, among others. In generally healthy patients, heart rate variability (HRV) of about 0.15 Hz to about 0.4 Hz is observed with respiration (breathing), with heart rate increasing during inspiration (inhalation) and decreasing during expiration (exhaling). HRV can decrease or increase greatly during meditation, and can increase by the practice of slow, paced breathing. Observers have noted a correlation between respiration-related HRV of about 0.15 Hz to about 0.4 Hz and physical health, including greater immune function, lower incidence of cardiac arrhythmia, and a greater prevalence of commonly-preferred emotional states (e.g., more "happiness" and less "sadness") relative to persons having respiration-related HRV below 0.15 Hz. Consequently, it may be beneficial for the patient to begin paced breathing during the pulse burst. Further, it may improve the efficacy of the exogenous electrical signal if the pulses are triggered while the patient is performing paced breathing. The beneficial effects of the paced breathing coupled with the therapeutic effects of the microbursts may increase the efficacy of the stimulation. Respiration-related HRV can be determined by monitoring heart rate or electrocardiography and calculating intervals between heart beats or particular points in consecutive cardiac cycles, such as consecutive R-waves. The variations in HRV can be used to indicate periods when the R-R interval is decreasing (corresponding to inspiration as the heart rate accelerates, thus reducing the duration of R-R interval relative to the prior R-R interval) or increasing (corresponding to expiration as the heart rate decelerates, thus increasing the R-R interval duration relative to the prior R-R interval). Alternatively, the IMD system 100 may detect the high frequency (0.18-0.4 Hz) component of the HRV power spectrum to determine when inspiration occurs. It will be appreciated that different techniques to detect cardiac cycles and respiration may be used, including separate sensors for heart rate and breathing, and that all such techniques are within the scope of the present invention.

In one embodiment, the IMD 100 applies a therapeutic electrical signal to the cranial nerve, such as the vagus nerve 127, at a point in the cardiac cycle correlated with increased afferent conduction on the cranial nerve, such as the vagus nerve 127. This may be done by sensing electrical activity on the vagus nerve and initiating the therapeutic electrical signal when the electrical activity increases. Without being bound by theory, since it is believed that increased electrical activity corresponds with inspiration and/or appropriate portions of the cardiac cycle, such a technique could result in supplementing the endogenous central vagal activity relevant to the patient's medical condition with the therapeutic, exogenous electrical signal.

In one embodiment, the IMD 100 applies an electrical signal to the cranial nerve, such as the vagus nerve 127, at a point in the cardiac cycle when applying the signal increases heart rate variability. In one further embodiment, the IMD 100 applies an electrical signal to the cranial nerve, such as the vagus nerve 127, beginning at a point from about 10 msec to about 800 msec after an R-wave of the patient's ECG during expiration (exhalation) by the patient.

In one embodiment, the IMD 100 does not apply an electrical signal to the cranial nerve, such as the vagus nerve 127, at a point during the cardiac cycle correlated with increased efferent conduction on the cranial nerve.

In one embodiment, stimulation may be applied to generate efferent electrical activity on the nerve, which refers to signals traveling on a nerve in a direction away from the central nervous system. In another embodiment, a "blocking" type of electrical signal may be employed using the IMD 100, such that both afferent and efferent electrical activity on the nerve is prevented from traveling further. Thus, the IMD 100 may operate to "silence" the vagus nerve.

Further, or alternatively, afferent stimulation may also be performed, wherein afferent fibers are stimulated while efferent fibers are not stimulated or are blocked. Afferent stimulation may be especially potent at times when the nerve conducts a relatively large number of afferent signals. For the vagus nerve, an example of such a time is about 10 msec to about 800 msec after the R-wave of the cardiac cycle.

In addition to electrical signals to generate efferent or afferent electrical activity on the nerve, the blocking type of stimulation described above may also be applied to the nerve. Efferent blocking may be realized by enhancing the hyper polarization of a stimulation signal, as described below. Embodiments of the present invention may employ the IMD 100 to perform afferent or efferent stimulation in combination with signal blocking, in order to treat medical conditions. Using the stimulation from the IMD 100, cranial nerve portions may be inhibited such that blocking of action potentials is achieved, wherein the various portions of the cranial nerve may also be stimulated to affect a mechanism in the patients' body.

The electrical stimulation treatment described herein may be used to treat a medical condition separately, or in combination with another type of treatment. For example, electrical stimulation treatment may be applied in combination with a chemical agent, such as various drugs, to treat various medical conditions. Therefore, various drugs may be taken by a patient, wherein the effects of these drugs may be enhanced by providing electrical stimulation to various portions of the nerves described herein to treat medical conditions. Further, the electrical stimulation may be performed in combination with treatment(s) relating to a biological or chemical agent. Therefore, drug therapy may be enhanced by the application of the stimulation provided by the IMD 100. The electrical stimulation treatment may also be performed in combination with other types of treatment, such as transcranial magnetic stimulation (TMS) treatment. Combining the electrical stimulation with the chemical, magnetic, or biological treatments, side effects associated with certain drugs or biological agents may be reduced.

Figure 2A:
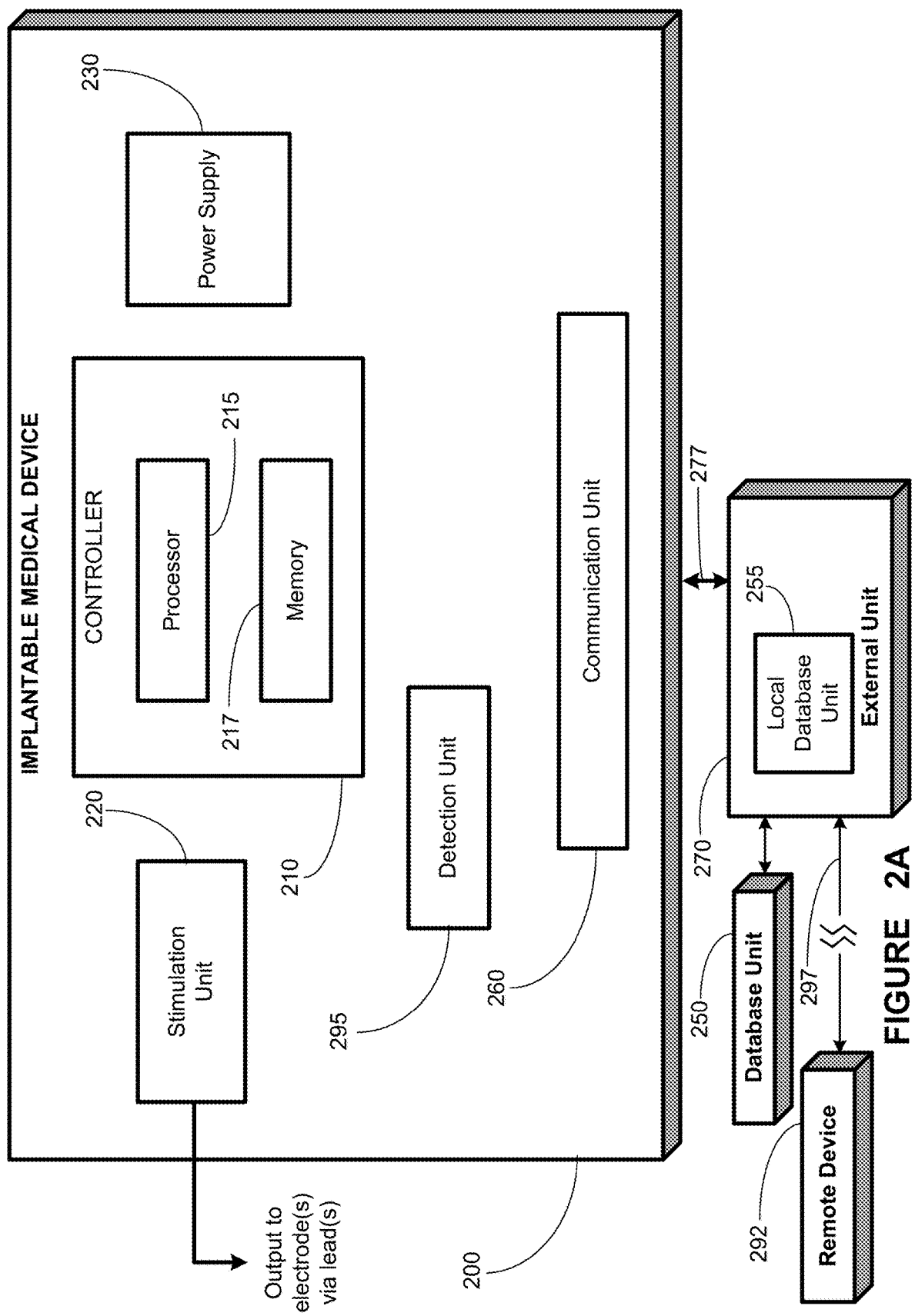
FIG. 2A is a block diagram of a medical device system that includes an implantable medical device and an external device for providing a patient management system for the implantable medical device, in accordance with one illustrative embodiment of the present invention.

Turning now to FIG. 2, a block diagram depiction of the IMD 200 is provided, in accordance with one illustrative embodiment of the present invention. The IMD 200 (such as generator 110 from FIG. 1) may comprise a controller 210 capable of controlling various aspects of the operation of the IMD 200. The controller 210 is capable of receiving internal data or external data and causing a stimulation unit 220 to generate and deliver an electrical signal to target tissues of the patient's body for treating a medical condition. For example, the controller 210 may receive manual instructions from an operator externally, or may cause the electrical signal to be generated and delivered based on internal calculations and programming. The controller 210 is capable of affecting substantially all functions of the IMD 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM) dynamic random access memory (DRAM), electrically erasable programmable read-only memory (EEPROM), flash memory, etc.

The IMD 200 may also comprise a stimulation unit 220 capable of generating and delivering electrical signals to one or more electrodes via leads. A lead assembly such as lead assembly 122 (FIG. 1) may be coupled to the IMD 200. Therapy may be delivered to the leads comprising the lead assembly 122 by the stimulation unit 220 based upon instructions from the controller 210. The stimulation unit 220 may comprise various circuitry, such as electrical signal generators, impedance control circuitry to control the impedance "seen" by the leads, and other circuitry that receives instructions relating to the delivery of the electrical signal to tissue. The stimulation unit 220 is capable of delivering an electrical signal over the leads comprising the lead assembly 122.

The IMD 200 may also comprise a power supply 230. The power supply 230 may comprise a battery, voltage regulators, capacitors, etc., to provide power for the operation of the IMD 200, including delivering the therapeutic electrical signal. The power supply 230 comprises a power source that in some embodiments may be rechargeable. In other embodiments, a non-rechargeable power source may be used. The power supply 230 provides power for the operation of the IMD 200, including electronic operations and the electrical signal generation and delivery functions. The power supply 230 may comprise a lithium/thionyl chloride cell or a lithium/carbon monofluoride (LiCFx) cell. Other battery types known in the art of implantable medical devices may also be used.

The IMD 200 may also comprise a communication unit 260 capable of facilitating communications between the IMD 200 and various devices. In particular, the communication unit 260 is capable of providing transmission and reception of electronic signals to and from an external unit 270, such as computer 150 and wand 155 that may comprise an ED (FIG. 1). The communication unit 260 may include hardware, software, firmware, or any combination thereof.

The IMD 200 also comprises a detection unit 295 that is capable of detecting various patient parameters. For example, the detection unit 295 may comprise hardware, software, or firmware that is capable of obtaining and/or analyzing data relating to one or more body parameters of the patient, such as heart rate, cardiac cycle data, and/or respiratory cycle data. Based upon the data obtained by the detection unit 295, the IMD 200 may deliver the electrical signal to a portion of the vagus nerve to treat epilepsy, depression or other medical conditions. In one embodiment, the detection unit 295 may be capable of detecting a feedback response from the patient. The feedback response may include a magnetic signal input, a tap input, a wireless data input to the IMD 200, etc. The feedback may be indicative of a pain and/or noxious threshold, wherein the threshold may be the limit of tolerance of discomfort for a particular patient. The term "patient parameters" may refer to, but is not limited to, various body parameters, which may in some embodiments involve sensors coupled to the IMD 200.

In another embodiment, the detection unit 295 may comprise hardware, software, or firmware that is capable of obtaining and/or analyzing data relating to one or more body parameters of the patient's cardiac cycle. Based upon the data obtained by the detection unit 295, the IMD 200 may deliver the electrical signal to a portion of the vagus nerve at one or more particular points in the cardiac cycle to treat epilepsy, depression or other medical conditions.

The external unit 270 may be an ED that is capable of programming electrical signal parameters of the IMD 200. In one embodiment, the external unit 270 is a computer system capable of executing a data-acquisition program. The external unit 270 may be controlled by a healthcare provider, such as a physician, at a base station in, for example, a doctor's office. In alternative embodiments, the external unit 270 may be controlled by a patient in a system providing less control over the operation of the IMD 200 than another external unit 270 controlled by a healthcare provider. Whether controlled by the patient or by a healthcare provider, the external unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, etc. The external unit 270 may download various parameters and program software into the IMD 200 for programming the operation of the IMD, and may also receive and upload various status conditions and other data from the IMD 200. Communications between the external unit 270 and the communication unit 260 in the IMD 200 may occur via a wireless or other type of communication, represented generally by line 277 in FIGS. 2A and 2B. This may occur using, e.g., wand 155 (FIG. 1) to communicate by RF energy with a generator 110. Alternatively, the wand may be omitted in some systems, e.g., systems in which external unit 270 operates in the MICS bandwidths.

In one embodiment, the external unit 270 may comprise a local database unit 255. Optionally or alternatively, the external unit 270 may also be coupled to a database unit 250, which may be separate from external unit 270 (e.g., a centralized database wirelessly linked to a handheld external unit 270). The database unit 250 and/or the local database unit 255 are capable of storing various patient data. This data may comprise patient parameter data acquired from a patient's body and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions using the external unit 270, which may include obtaining and/or analyzing data from the IMD 200 and/or data from the database unit 250 and/or the local database unit 255. The database unit 250 and/or the local database unit 255 may store various patient data such as heart rate data, cardiac cycle data (such as R-R interval data), respiratory cycle information, etc.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Figure 3:
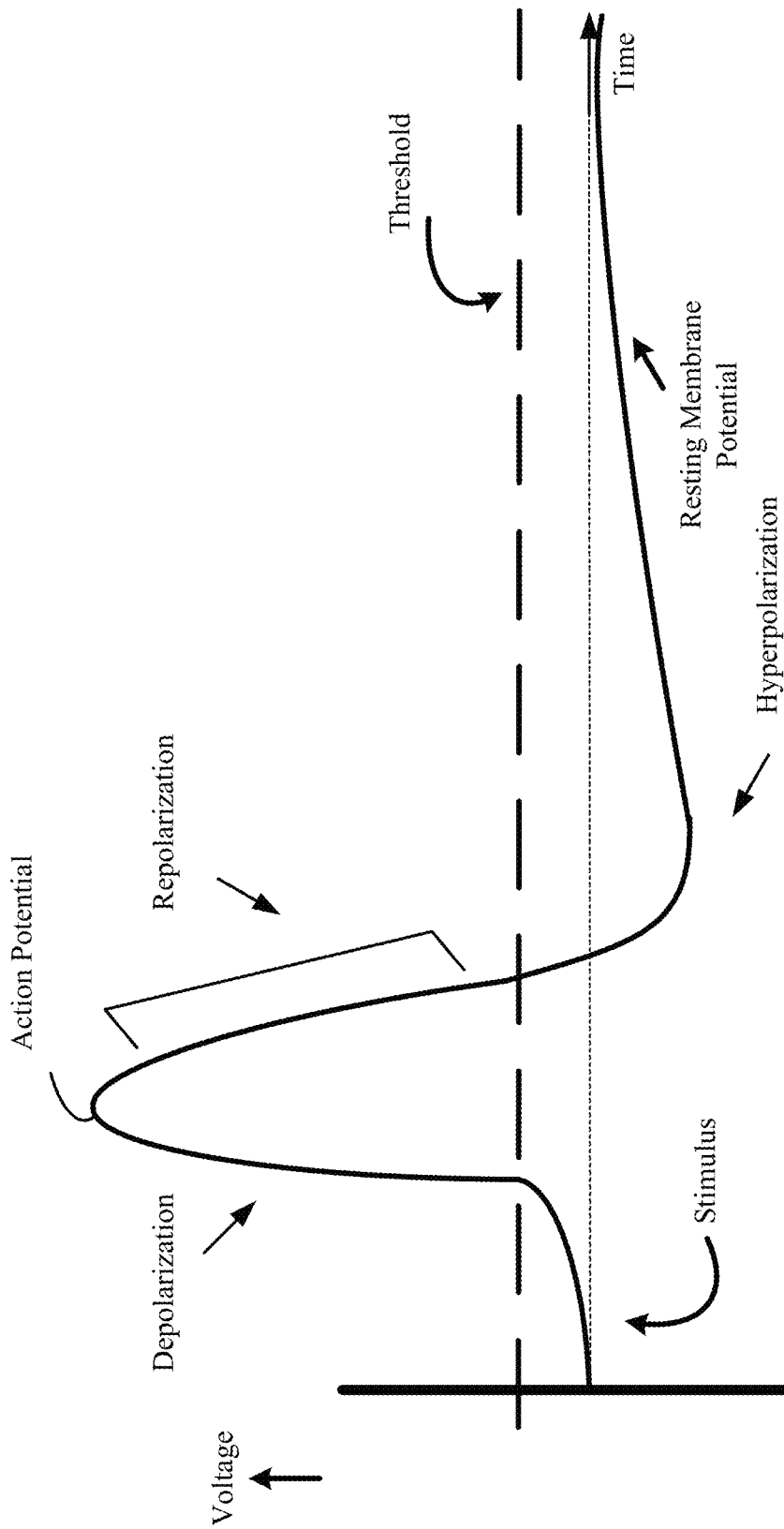
FIG. 3 illustrates an exemplary electrical signal of a firing neuron as a graph of voltage at a given location at particular times in response to application of an electrical signal to the nerve by the neurostimulator of FIG. 2, in accordance with one illustrative embodiment of the present invention.

FIG. 3 provides a stylized depiction of an exemplary electrical signal of a firing neuron as a graph of voltage at a given point on the nerve at particular times during the propagation of an action potential along the nerve, in accordance with one embodiment of the present invention. A typical neuron has a resting membrane potential of about −70 mV, maintained by transmembrane ion channel proteins. When a portion of the neuron reaches a firing threshold of about −55 mV, the ion channel proteins in the locality allow the rapid ingress of extracellular sodium ions, which depolarizes the membrane to about +30 mV. The wave of depolarization then propagates along the neuron. After depolarization at a given location, potassium ion channels open to allow intracellular potassium ions to exit the cell, lowering the membrane potential to about −80 mV (hyperpolarization). About 1 msec is required for transmembrane proteins to return sodium and potassium ions to their starting intra- and extracellular concentrations and allow a subsequent action potential to occur.

Figure 9:
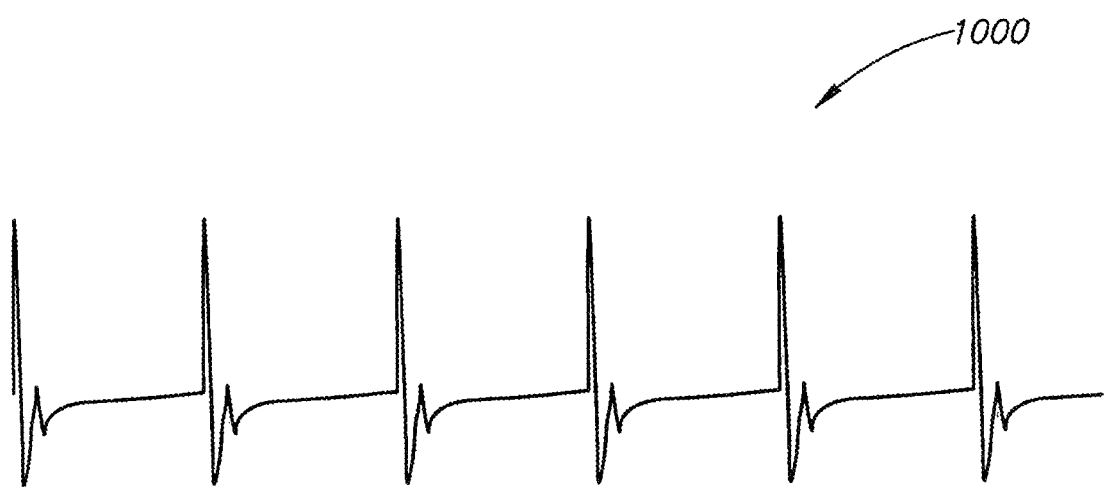
FIG. 9 illustrates a second pulsed electrical signal that is not a microburst signal.

Referring again to FIG. 1, the IMD 100 may generate a pulsed electrical signal in embodiments of the present invention for application to a cranial nerve such as vagus nerve 127 according to one or more programmed parameters. In one embodiment, the electrical signal may be a conventional vagus nerve therapeutic electrical signal defined by a plurality of parameters such as current magnitude, pulse width, frequency, on-time and off-time. In another embodiment, the electrical signal may be a microburst signal defined by a plurality of parameters such as an interburst period, a number of a number of pulses per burst, an interpulse interval, a burst duration, a current magnitude, a pulse width, an on-time, and an off-time. In yet another embodiment illustrated in FIG. 9, the electrical signal may comprise a first time period in which conventional vagus nerve therapeutic electrical signals 1000 are applied to the nerve, and a second time period in which microburst electrical signals are applied to the nerve. In a still further embodiment, conventional and microburst signals are alternated with a defined off-time in a conventional on-time and a microburst on-time. Thus a 30 second burst of a conventional VNS signal may be followed by 5 minutes off-time, followed by a 1 minute period of microburst stimulation, followed by a 5 minute off-time, after which the process repeats itself.

Figure 4C:
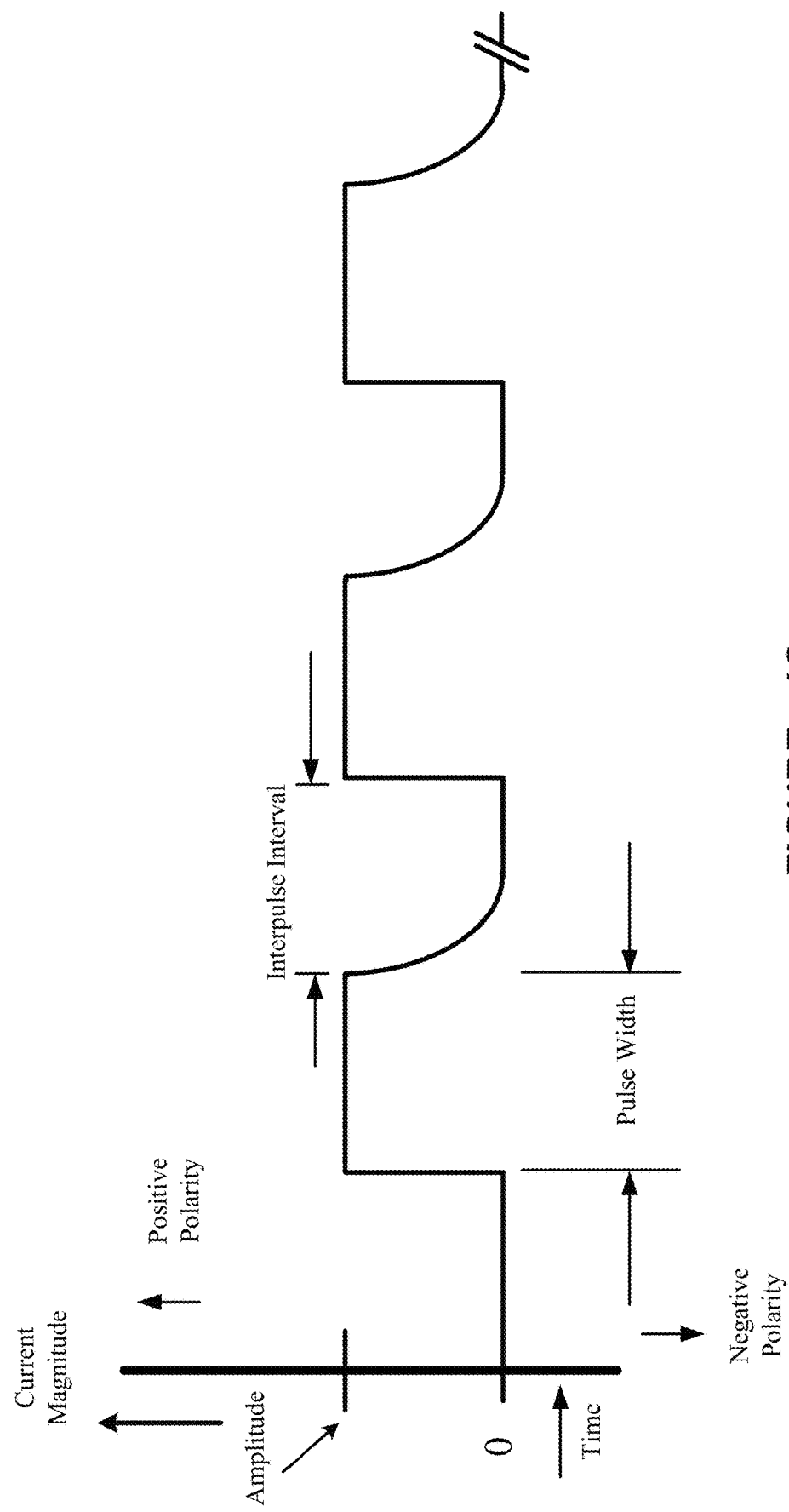

Exemplary pulse waveforms in accordance with one embodiment of the present invention are shown in FIGS. 4A-4C. Pulse shapes in electrical signals according to the present invention may include a variety of shapes known in the art including square waves, biphasic pulses (including active and passive charge-balanced biphasic pulses), triphasic waveforms, etc. In one embodiment, the pulses comprise a square, biphasic waveform in which the second phase is a charge-balancing phase of the opposite polarity to the first phase.

In addition to conventional programmed or random off-time periods (and whether conventional or microburst stimulation is applied), the duration of a period of "off-time" in embodiments of the present invention may be varied with changes in the patient's cardiac cycle. In one embodiment, the "off-time" begins about 10 msec to about 800 msec after the onset of the R-wave of a patient's cardiac cycle and ends at the onset of the R-wave of a later cardiac cycle of the patient, such as the next cardiac cycle.

In one embodiment, the present invention may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode may be coupled to each of the vagus nerves 127 or a branch of either vagus nerve. The term "operatively" coupled may include directly or indirectly coupling. Each of the nerves in this embodiment or others involving two or more cranial nerves may be stimulated according to particular activation modalities that may be independent between the two nerves.

Another activation modality for stimulation is to program the output of the IMD 100 to the maximum amplitude which the patient may tolerate. The stimulation may be cycled on and off for a predetermined period of time followed by a relatively long interval without stimulation. Where the cranial nerve stimulation system is completely external to the patient's body, higher current amplitudes may be needed to overcome the attenuation resulting from the absence of direct contact with the cranial nerve and the additional impedance of the skin of the patient. Although external systems typically require greater power consumption than implantable ones, they have an advantage in that their batteries may be replaced without surgery.

Returning to systems for providing cranial nerve stimulation, such as that shown in FIGS. 1 and 2, stimulation may be provided in either non-feedback or feedback modalities. Where cranial nerve stimulation is provided based solely on programmed off-times and on-times, the stimulation may be referred to as passive, inactive, or non-feedback stimulation. In contrast, stimulation may be triggered by one or more feedback loops according to changes in the body or mind of the patient. This stimulation may be referred to as active or feedback-loop stimulation. In one embodiment, feedback-loop stimulation may be manually-triggered stimulation, in which the patient manually causes the activation of a pulse burst outside of the programmed on-time/off-time cycle. The patient may manually activate the IMD 100 to stimulate the vagus nerve 127 to treat an acute episode of a medical condition. The patient may also be permitted to alter the intensity of the signals applied to the cranial nerve within limits established by the physician.

Patient activation of an IMD 100 may involve use of an external control magnet for operating a reed switch in an implanted device, for example. Certain other techniques of manual and automatic activation of implantable medical devices are disclosed in U.S. Pat. No. 5,304,206 to Baker, Jr., et al., assigned to the same assignee as the present application ("the '206 patent"). According to the '206 patent, means for manually activating or deactivating the electrical signal generator 110 may include a sensor such as piezoelectric element mounted to the inner surface of the generator case and adapted to detect light taps by the patient on the implant site. One or more taps applied in fast sequence to the skin above the location of the electrical signal generator 110 in the patient's body may be programmed into the implanted medical device 100 as a signal for activation of the electrical signal generator 110. Two taps spaced apart by a slightly longer duration of time may be programmed into the IMD 100 to indicate a desire to deactivate the electrical signal generator 110, for example. The patient may be given limited control over operation of the device to an extent which may be determined by the program dictated or entered by the attending physician. The patient may also activate the IMD 100 using other suitable techniques or apparatus.

In some embodiments, feedback stimulation systems other than manually-initiated stimulation may be used in the present invention. A cranial nerve stimulation system may include a sensing lead coupled at its proximal end to a header along with a stimulation lead and electrode assemblies. A sensor may be coupled to the distal end of the sensing lead. The sensor may include a cardiac cycle sensor. The sensor may also include a nerve sensor for sensing activity on a nerve, such as a cranial nerve, such as the vagus nerve 127.

In one embodiment, the sensor may sense a body parameter that corresponds to a symptom of a medical condition. If the sensor is to be used to detect a symptom of the medical condition, a signal analysis circuit may be incorporated into the IMD 100 for processing and analyzing signals from the sensor. Upon detection of the symptom of the medical condition, the processed digital signal may be supplied to a microprocessor in the IMD 100 to trigger application of the electrical signal to the cranial nerve, such as the vagus nerve 127. In another embodiment, the detection of a symptom of interest may trigger a stimulation program including different stimulation parameters from a passive stimulation program. This may entail providing a higher current stimulation signal or providing a higher ratio of on-time to off-time.

Figure 5:
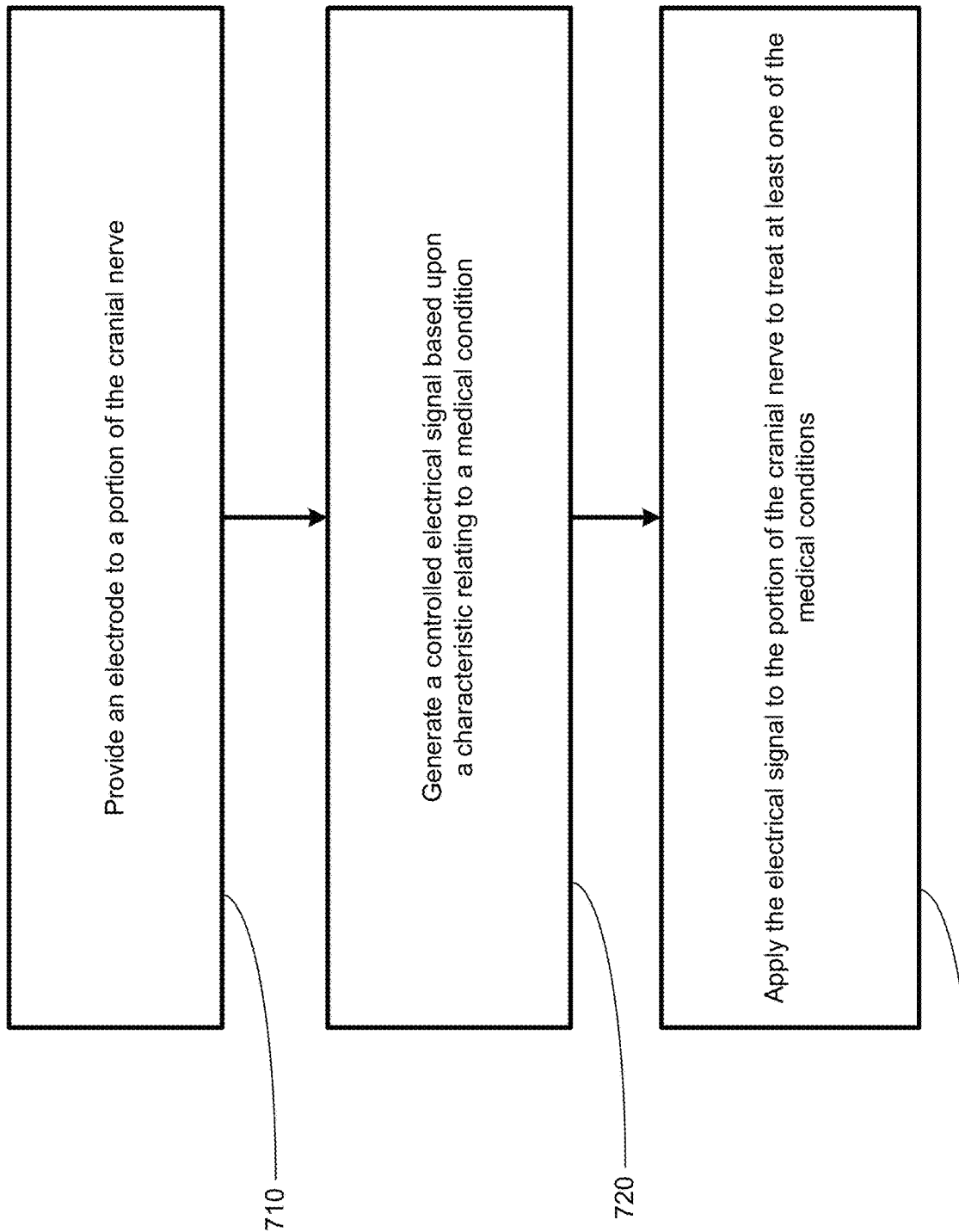
FIG. 5 illustrates a flowchart depiction of a method for treating a medical condition, in accordance with an illustrative embodiment of the present invention.

Turning now to FIG. 5, a flowchart depiction of a method for treating a medical condition, in accordance with one illustrative embodiment of the present invention is provided. An electrode may be coupled to a portion of a cranial nerve to perform a stimulation function or a blocking function to treat a medical condition. In one embodiment, one or more electrodes may be positioned in electrical contact or proximate to a portion of the cranial nerve to deliver a stimulation signal to the portion of the cranial nerve (block 710). The electrodes may be operatively coupled to at least one of main trunk of the right or left vagus nerve, or any branch thereof. The IMD 100 may then generate a controlled electrical signal, based upon one or more characteristics relating to the medical condition(s) of the patient (block 720). This may include a predetermined electrical signal that is preprogrammed based upon a particular condition of a patient. The term "medical condition" may include epilepsy or depression, among others. For example, a physician may pre-program the type of stimulation to provide (e.g., conventional stimulation, microburst stimulation, or combination conventional/microburst stimulation) in order to treat the patient based upon the medical condition of the patient. The IMD 100 may then generate a signal, such as a controlled-current pulse signal, to affect one or more portions of the neurological system of a patient.

The IMD 100 may then deliver the stimulation signal to the portion of the cranial nerve (block 730). The application of the electrical signal may be delivered to the main trunk of the right or left vagus nerve, or any branch thereof. In one embodiment, application of the stimulation signal may be designed to generate afferent electrical activity on the vagus nerve 127. Further, the stimulation by the IMD 100 may reduce incidents or symptoms relating to a medical condition. Application of the stimulation signal may be controlled so that the signal is applied during periods of the cardiac cycle correlated with increased afferent traffic on the cranial nerve.

In another embodiment, application of the stimulation signal may be designed to promote a blocking effect relating to a signal that is being sent from the brain, to treat the medical condition. This may be accomplished by delivering a particular type of controlled electrical signal, such as a controlled current signal to the cranial nerve. In yet another embodiment, afferent fibers may also be stimulated in combination with an efferent blocking to treat a medical condition.

Additional functions, such as a detection process, may be alternatively employed with the embodiment of the present invention. The detection process may be employed such that an external detection or an internal detection of a bodily function may be used to adjust the operation of the IMD 100.

Figure 6:
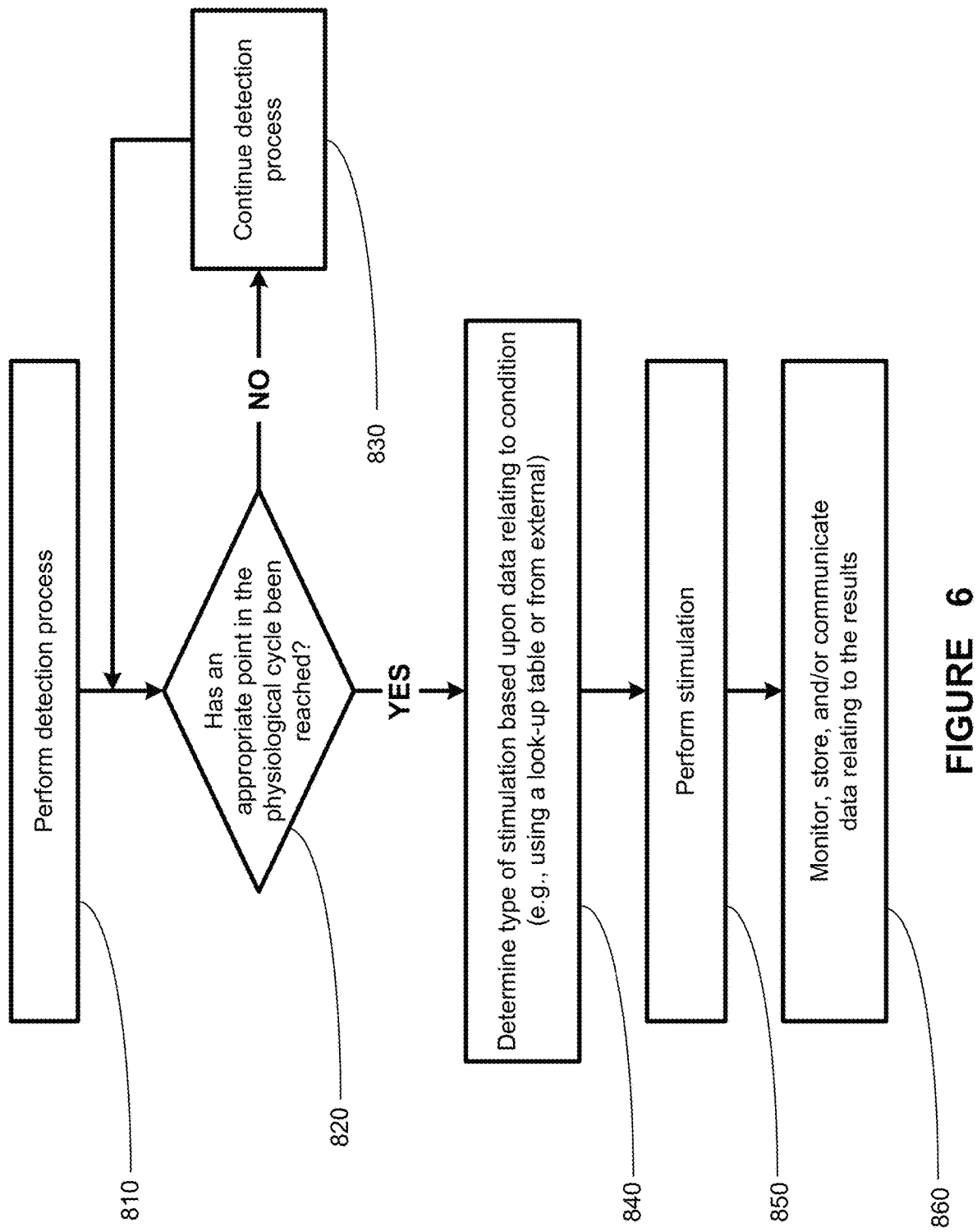
FIG. 6 illustrates a flowchart depiction of an alternative method for treating a medical condition, in accordance with an alternative illustrative embodiment of the present invention.

Turning now to FIG. 6, a block diagram depiction of a method in accordance with an alternative embodiment of the present invention is illustrated. The IMD 100 may perform a detection process, which may include checking a database for physiological data, such as data indicative of the patient's cardiac cycle (block 810). Data from the database may be used for determining the timing of the delivery of stimulation signals, e.g. timing delivery based on the patient's cardiac cycle. The detection process may encompass detecting a variety of types of characteristics of the cardiac cycle of the patient. A more detailed depiction of the steps for performing the detection process is provided in FIG. 7, and accompanying description below. Upon performing the detection process, the IMD 100 may determine whether an appropriate point in the cardiac cycle has been reached (block 820). Upon a determination that an appropriate point in the cardiac cycle has not been reached, the detection process is continued (block 830).

Upon a determination that an appropriate time in the cardiac cycle has been reached, a determination as to the type of stimulation based upon data relating to the medical condition is made (block 840). The type of stimulation may be determined in a variety of manners, such as performing a look-up in a look-up table that may be stored in the memory 217. Alternatively, the type of stimulation may be determined by an input from an external source, such as the external unit 270 or an input from the patient. Further, determination of the type of stimulation may also include determining the location as to where the stimulation is to be delivered. Accordingly, the selection of particular electrodes, which may be used to deliver the stimulation signal, is made.

Upon determining the type of stimulation to be delivered, the IMD 100 performs the stimulation by applying the electrical signal to one or more selected electrodes (block 850). Upon delivery of the stimulation, the IMD 100 may monitor, store, or compute the results of the stimulation (block 860). For example, based upon the calculation, a determination may be made that adjustment(s) to the type of signal to be delivered for stimulation, may be performed. Further, the calculations may reflect the need to deliver additional stimulation. Additionally, data relating to the results of stimulation may be stored in memory 217 for later extraction or further analysis. Also, in one embodiment, real time or near real time communications may be provided to communicate the stimulation result or the stimulation log to an external unit 270.

Figure 7:
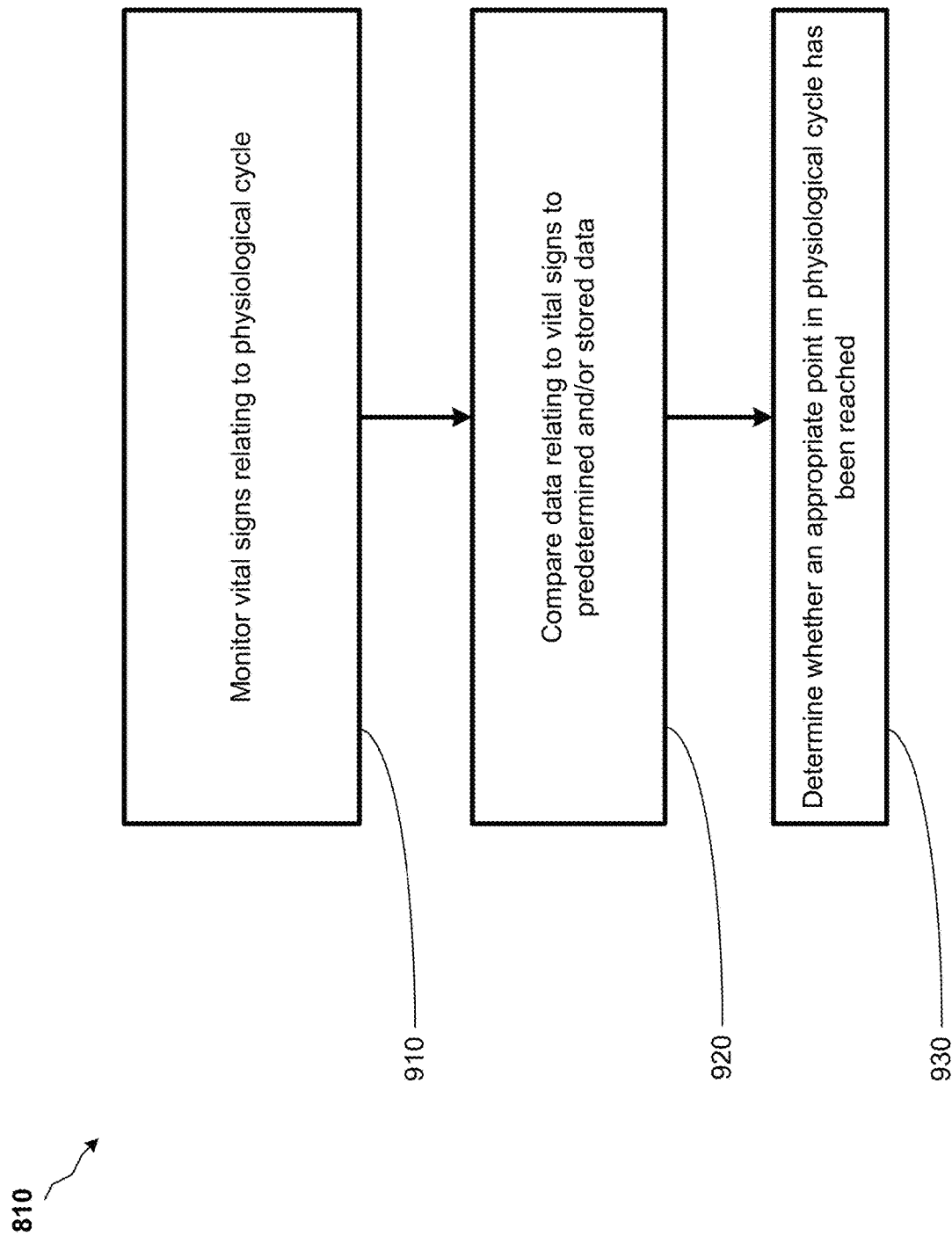
FIG. 7 depicts a more detailed flowchart depiction of the step of performing a detection process of FIG. 6, in accordance with an illustrative embodiment of the present invention.

Turning now to FIG. 7, a more detailed block diagram depiction of a particular embodiment of the step of performing the detection process of block 810 in FIG. 6, is illustrated. The system 100 may monitor one or more signals relating to the cardiac cycle of the patient (block 910). This detection may be made by sensors residing inside the human body, which may be operatively coupled to the IMD 100. In a particular embodiment, the sensors may be located in the IMD 100. In another embodiment, these signals may be detected by external means and may be provided to the IMD 100 from an external device via the communication unit 260.

Upon acquisition of various signals, a comparison may be performed comparing the data relating to the real-time signals or stored physiological data to predetermined and/or stored data (block 920). For example, an ECG may be compared to various benchmark ECGs to determine whether a portion of the cardiac cycle correlated with increased afferent vagus nerve conduction has been reached. Based upon the comparison of the collected data with theoretical, stored thresholds, the IMD 100 may determine whether an appropriate time to commence an on-time (i.e., a time to apply the electrical signal to the cranial nerve) has been reached (block 930). Based upon the determination described in FIG. 7, the IMD 100 may continue to determine whether the medical condition is sufficiently significant to perform treatment, as described in FIG. 6.

Additionally, external devices may perform such calculation and communicate the results or accompanying instructions to the IMD 100. The IMD 100 may also determine the specific cranial nerve(s), or the location or branch of the nerve(s), to stimulate. The IMD 100 may also indicate the type of treatment to be delivered. For example, an electrical treatment alone or in combination with another type of treatment may be provided based upon the quantifiable parameter(s) that are detected. For example, a determination may be made that an electrical signal by itself is to be delivered. Alternatively, based upon a particular type of medical condition, a determination may be made that an electrical signal, in combination with a magnetic signal, such as transcranial magnetic stimulation (TMS) may be performed. Stimulation can be induced by light such as from a laser.

In addition to electrical or magnetic stimulation, a determination may be made whether to deliver a chemical, biological, or other type of treatment(s) in combination with the electrical stimulation provided by the IMD 100. In one example, electrical stimulation may be used to enhance the effectiveness of a chemical agent. Therefore, various drugs or other compounds may be delivered in combination with an electrical stimulation or a magnetic stimulation. Based upon the type of stimulation to be performed, the IMD 100 delivers the stimulation to treat various medical conditions.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method of treating a medical condition in a patient comprising:
   detecting a portion of a cardiac cycle of the patient;
   detecting a portion of a respiratory cycle of the patient based on using a high frequency component of a heart rate variability power spectrum to determine when inspiration occurs;
   applying to a vagus nerve of the patient, in response to the detecting of the portion of the cardiac cycle and the inspiration occurrence, a pulsed electrical signal comprising a plurality of microbursts where the pulsed electrical signal is applied during inspiration,
   wherein each microburst is characterized by:
      from 2 to 20 pulses per microburst;
      an interpulse interval between adjacent pulses of the microburst is about 1 to about 20 milliseconds; and
      a microburst duration of less than 1 second; and
   wherein each microburst is separated from an adjacent microburst by an interburst period of at least 100 milliseconds.

2. The method of claim 1, wherein the detecting a portion of the cardiac cycle of the patient comprises determining a heart rate variability (HRV) parameter, and wherein applying the pulsed electrical signal to the vagus nerve comprises applying the pulsed electrical signal to the vagus nerve in response to the determined HRV parameter.

3. The method of claim 2, further comprising increasing the heart rate variability parameter of the patient by applying the pulsed electrical signal to the vagus nerve.

4. The method of claim 1, wherein the detecting a portion of the cardiac cycle of the patient comprises determining an inhibition phase of the cardiac cycle and the applying further comprises not applying the pulsed electrical signal during the inhibition phase of the cardiac cycle.

5. The method of claim 4, wherein applying the pulsed electrical signal comprises applying the pulsed electrical signal after a delay period following detection of an R-wave of the cardiac cycle of the patient, and not applying the pulsed electrical signal for a period of from a remaining portion of the same cardiac cycle to one or more subsequent cardiac cycles.

6. The method of claim 1, wherein the detecting a portion of the cardiac cycle of the patient comprises detecting at least a portion of the cardiac cycle selected from a group consisting of a P wave, an R wave, an R-R interval, a QRS complex, a T wave, and an entire PQRST cycle.

7. The method of claim 1, further comprising sensing a temperature of the patient and wherein applying comprises applying the pulsed electrical signal in response to the temperature of the patient.

8. The method of claim 1, further comprising applying a second pulsed electrical signal to the vagus nerve without reference to the cardiac cycle of the patient.

9. The method of claim 8, wherein the second pulsed electrical signal is not a microburst signal.

10. The method of claim 1, wherein applying the pulsed electrical signal comprises applying the pulsed electrical signal after a delay period following detection of a beginning of inspiration, and not applying the pulsed electrical signal for a period from a remaining portion of the same respiratory cycle to one or more subsequent respiratory cycles.

11. A system for treating a medical condition in a patient comprising:
   a sensor configured for sensing at least a portion of a cardiac cycle of the patient and
   a respiratory cycle of the patient;
   a lead assembly comprising at least one electrode configured for being coupled to a vagus nerve of the patient;
   an implantable medical device coupled to the lead assembly and the sensor and comprising:
      a detection unit coupled to the sensor configured for detecting the portion of the cardiac cycle of the patient and an inspiration phase of the respiratory cycle of the patient;
      a stimulation unit capable of generating and delivering a pulsed electrical signal comprising a plurality of microbursts to the at least one electrode in response to the detection unit detecting the portion of the cardiac cycle and the inspiration phase of the respiratory cycle of the patient, wherein each microburst is characterized by:

from 2 to 20 pulses per microburst;
an interpulse interval between adjacent pulses of the microburst is about 1 to about 20 milliseconds; and
a microburst duration of less than 1 second; and wherein each microburst is separated from an adjacent microburst by an interburst period of at least 100 milliseconds; and
a controller configured for controlling the implantable medical device to apply the pulsed electrical signal comprising the plurality of microbursts to the vagus nerve of the patient during the inspiration phase using the at least one electrode.

12. The system of claim 11, wherein the detection unit is further configured to determine a heart rate variability (HRV) parameter, and wherein the stimulation unit is further configured for generating and delivering the pulsed electrical signal to the vagus nerve in response to the determined HRV parameter.

13. The system of claim 11, wherein the detection unit is further configured to utilize a high frequency component of a HRV power spectrum to determine when inspiration occurs.

* * * * *